United States Patent
Horie et al.

(10) Patent No.: US 6,586,178 B1
(45) Date of Patent: Jul. 1, 2003

(54) NUCLEIC ACID PROBE

(75) Inventors: Ryuichi Horie, Kanagawa (JP);
Takahiko Ishiguro, Kanagawa (JP);
Takumi Tokunaga, Kanagawa (JP);
Takashi Yamamoto, Yamaguchi (JP);
Juichi Saitoh, Kanagawa (JP);
Toshitaka Taya, Kanagawa (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 09/519,859

(22) Filed: Mar. 6, 2000

(30) Foreign Application Priority Data

Mar. 5, 1999 (JP) .......................... 11-058251

(51) Int. Cl.[7] .......................... C12Q 1/68; C12P 19/34; C07H 19/00; C07H 21/00; C07H 21/02
(52) U.S. Cl. .................. 435/6; 435/91.1; 435/91.2; 536/22.1; 536/23.1; 536/24.3
(58) Field of Search .................. 435/6, 91.1, 91.2; 536/22.1, 23.1, 24.3

(56) References Cited

U.S. PATENT DOCUMENTS

| 5,814,447 A | 9/1998 | Ishiguro et al. ............... 435/6 |
| 6,211,354 B1 | 4/2001 | Horie et al. ............... 536/24.3 |

FOREIGN PATENT DOCUMENTS

EP 0714907 * 5/1996

OTHER PUBLICATIONS

Matthews et al. "Review. Analytica;l Strategies for the Use of DNA Probes" Analytical Biochemistry, 169, pp. 1–25, 1988.*

Gait et al. Journal of Chemical Society 1979, pp. 1389–1394.*

Greenberg et al. Tetrahedron vol. 51, No: 1, pp. 29–38, 1995.*

Takahiko Ishiguro et al., Fluorescence detection of specific sequence of nucleic acids by oxazole yellow–linked oligonucleotides. Homogeneous quantitative monitoring of in vitro transcription, *Nucleic Acids Research*, vol. 24, No. 24, pp. 49893–4997 (1996).

Ryuichi Horie et al., "Intercalator–linked DNA probe having stereoregular 2–aminoethylphosphonatediester linkage," *Nucleic Acids Symposium Series* No. 39, pp. 39–40, (1998).

* cited by examiner

*Primary Examiner*—Jezia Riley
(74) *Attorney, Agent, or Firm*—Jacobson Holman PLLC

(57) ABSTRACT

A nucleic acid probe which is a single-stranded nucleic acid complementary to a specific nucleic acid sequence and is labeled so as to give off a measurable fluorescent signal on hybridization with a nucleic acid containing the specific nucleic acid sequence, wherein the 3' end of the probe is modified as represented by the following formula (1):

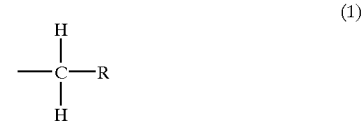

wherein R is —COOH, —CONH$_2$, —(CH$_2$)$_n$OH, —CH(OH)—CH$_2$OH, or —CH[(CH$_2$)$_n$—NHR$_1$]—CH$_2$OH, R$_1$ is H, a dye, or an amino protecting group such as Fmoc, and n is an integer of at least 1.

12 Claims, 5 Drawing Sheets

NUCLEIC ACID PROBE

NUCLEIC ACID PROBE

The present invention relates to a nucleic acid probe useful in the field of clinical diagnosis such as gene diagnosis and in the field of exploration of unknown genes and a method for qualitative or quantitative assay of a DNA or RNA containing a specific nucleic acid sequence as a target nucleic acid using the nucleic acid probe.

Qualitative or quantitative assays of a target nucleic acid containing a specific nucleic acid sequence (anticipated) in samples require high specificity, like assays of biogenic components. In assays specific for a target nucleic acid, a single-stranded oligonucleotide (a nucleic acid probe) which is complementary to a specific nucleic acid sequence in the target nucleic acid and sequence-specifically binds to the regional specific nucleic acid sequence in the target nucleic acid is used.

In assays of a target nucleic acid using a nucleic acid probe, it is common to link the nucleic acid probe to a spectroscopically detectable label which enables detection of the hybrid sequence-specifically formed between the nucleic acid probe and the target nucleic acid. Assays of a target nucleic acid using a nucleic acid probe also require high detection sensitivity. Especially, for example, in clinical samples for diagnoses of infectious diseases such as blood, target nucleic acids from viruses such as HCV and HIV are usually present in trace amounts. Therefore, use of a nucleic acid probe labeled with an enzyme together with a chemiluminescent substrate of the enzyme and use of a nucleic acid probe linked via a linker to a fluorescent intercalative dye which intercalates into base pairs of a double-stranded nucleic acid have been proposed.

In recent years, it is common to amplify a target nucleic acid by PCR (polymerase chain reaction) or the like in advance and then hybridize a nucleic acid probe with the amplified target nucleic acid with a view to increasing the sensitivity. Specifically, because a fluorescent intercalative dye-labeled nucleic acid probe as mentioned above characteristically obviates the need to use a support for separation of the unhybridized target nucleic acid from a mixture of a target nucleic acid and a nucleic acid probe in conventional assays of the target nucleic acid, the presence of such a fluorescent intercalative dye-labeled nucleic acid probe during an amplification reaction such as PCR makes it possible to measure a target nucleic acid during or after the amplification in a sealed vessel without addition of any reagents during a series of operations from amplification to measurement and obviate the possibility of contamination of other samples by aerosol generated from a sample in hand (JP-A-8-211050, Japanese Patent Application JP10-186434, EP-A-714986).

The above-mentioned amplification by PCR or the like in the presence of a nucleic acid probe produces an excellent effect of enabling assays in sealed vessels, which were impossible by conventional methods. However, customary amplification in the presence of a nucleic acid probe is accompanied by elongation of the nucleic acid probe from the 3' end, which can lead to a recognizable signal from the label even in the absence of the target nucleic acid.

For DNA amplification by PCR, it is known to introduce one or two bases in the 3' end of a nucleic acid probe uncomplementary to a target nucleic acid (JP-A-8-211050). But in the case of amplification of an RNA as the target nucleic acid comprising synthesis of a DNA complementary to the RNA using a primer and a reverse transcriptase along the RNA as the template, DNA elongation from a promoter primer partly complementary to the resulting complementary DNA triggered by their hybridization and subsequent large scale production of the target RNA by the action of an RNA polymerase on the resulting double-stranded DNA, it has been found that use of such a nucleic acid probe can result in a signal, though weak, from the label due to DNA elongation from the 3' end of the nucleic acid probe during the reverse transcription.

The object of the present invention is to provide a nucleic acid probe which does not undergo DNA elongation from the 3' end during nucleic acid amplification involving synthesis of a complementary nucleic acid using a target nucleic acid as the template such as the above-mentioned DNA and RNA amplification. Another object of the present invention is to realize nucleic acid amplification in the presence of a nucleic acid probe by using the nucleic acid probe.

In order to achieve the above-mentioned objects, according to claim 1 of the present application, the present invention provides a nucleic acid probe which is a single-stranded nucleic acid complementary to a specific nucleic acid sequence and is labeled so as to give off a measurable fluorescent signal on hybridization with a nucleic acid containing the specific acid sequence, wherein the 3' end of the probe is modified as represented by formula (1).

In order to achieve the above-mentioned objects, according to claim 2 of the present application, the present invention provides a method for qualitative or quantitative assay of a target nucleic acid containing a specific base sequence, which comprises amplifying the target nucleic acid in the presence of a single-stranded nucleic acid probe complementary to the specific nucleic acid sequence which is labeled so as to give off a measurable signal on hybridization with a nucleic acid containing the specific nucleic acid sequence and measuring the amplified target nucleic acid hybridized with the nucleic acid probe during and/or after the amplification, wherein the 3' end of the single-stranded nucleic acid probe is modified as represented by formula (2).

The nucleic acid probe of the present invention can be present during the after-mentioned procedure for nucleic acid amplification. A target nucleic acid can be measured with the nucleic acid probe of the present invention after or during amplification of the target nucleic acid.

The assay of a target nucleic acid is based on detection of the nucleic acid probe hybridized with a target nucleic acid. Therefore, the nucleic acid probe of the present invention has a spectroscopically detectable label such as an enzyme, a luminescent substance or a fluorescent substance. A fluorescent intercalative dye is particularly preferable as the label because the above-mentioned detection can be accomplished in a sealed vessel during or after amplification of a target nucleic acid.

Though any intercalative dye such as oxazole yellow, thiazole orange, ethidium bromide and acridine orange that changes its fluorescent characteristics on intercalation between base pairs in a double-stranded nucleic acid can be used without any particular restriction, thiazole orange or oxazole yellow is particularly preferable in view of the easiness of detection because they enhance their fluorescent intensities markedly upon intercalation. Use of a fluorescent intercalative dye as the label makes it possible to detect the target nucleic acid as described above without using a solid support for separation of the hybridized nucleic acid probe from the unhybridized nucleic acid probe.

The intercalative dye is linked to the nucleic acid probe via an appropriate linker.

The nucleic acid probe of the present invention is characterized by the 3' modification represented by formula (1) wherein R is —COOH, —CONH$_2$, —(CH$_2$)$_n$OH, —CH(OH)—CH$_2$OH or —CH[(CH$_2$)$_n$—NHR$_1$]—CH$_2$OH, R$_1$ is H, a dye, or an amino-protecting group such as Fmoc (9-fluorenylmethyloxycarbonyl), and n is an integer of at least 1.

Preparation of the nucleic acid probe of the present invention will be explained by taking a fluorescent intercalative dye-labeled nucleic acid probe as an example. Firstly, a DNA oligomer complementary to a specific nucleic acid sequence in the target nucleic acid is synthesized by a DNA synthesizer by using a solid phase represented by the following formula (3) or (4) as a starting material.

(3)

wherein R$_2$ is a hydroxyl-protecting group such as a DMTr (4,4'-dimethoxytrityl) group, CGP is a support such as Controlled pore grass or silica gel, and X is an arbitrary linker, (4)

wherein R$_3$ is a hydroxyl-protecting group such as a DMTr group, R$_4$ is —(CH$_2$)$_n$—, —CH(OH)—CH$_2$— or —CH[(CH$_2$)$_n$—NHR$_5$]—CH$_2$—, R$_5$ is H, a dye, or an amino-protecting group such as Fmoc, n is an integer of at least 1, CGP is a support such as Controlled pore grass or silica gel, and X is an arbitrary linker.

The arbitrary linker, X, in the above formula (3) or (4) may be any compound that is unsusceptible to the reactions carried out in the DNA synthesizer without any particular restriction.

After the DNA synthesis, the DNA oligomer is released from the support with a modified 3' end represented by the following formula (5) by conventional treatment with 28% ammonia or the like with accompanying deprotection of nucleic acid bases and phosphate groups.

(5)

wherein R is —COOH, —CONH$_2$, —(CH$_2$)$_n$OH, —CH(OH)—CH$_2$OH or —CH[(CH$_2$)$_n$—NHR$_1$]—CH$_2$OH, R$_1$ is H, a dye, or an amino-protecting group such as Fmoc, and n is an integer of at least 1.

Then, the resulting DNA oligomer is linked to a fluorescent intercalative dye in accordance with JP-A=8-211050 or EP-A-714986.

The presence of the nucleic acid probe of the present invention during amplification of a target nucleic acid is suitable for measurement of the target nucleic acid during and/or after the amplification. The nucleic acid probe of the present invention is the most effective in amplification involving DNA synthesis or reverse transcription into DNA using a target nucleic acid as the template, such as DNA amplification by PCR through elongation of primers along a target nucleic acid (DNA) as the template by the action of a DNA polymerase, or amplification of an RNA as the target nucleic acid comprising synthesis of a DNA complementary to the RNA using a primer and a reverse transcriptase along the RNA as the template, DNA elongation from a promoter primer partly complementary to the resulting complementary DNA triggered by their hybridization and subsequent large scale production of the target RNA by the action of an RNA polymerase on the resulting double-stranded DNA.

There is no particular restriction on the method for RNA amplification mentioned later as long as it involves DNA synthesis or reverse transcription into DNA using a target nucleic acid as the template, though various methods such as the NASBA (Nucleic Acid Sequence-Based Amplification) method, the 3SR (Self-Sustained Sequence Replication) method and the method disclosed in Japanese Patent Application JP10-186434 may be mentioned.

As described above, the presence of the nucleic acid probe of the present invention during the above-mentioned amplification makes it possible to detect and quantify the target nucleic acid during or after the amplification of the target nucleic acid. In this case, because it is possible to conduct a series of operations from amplification to measurement of the target nucleic acid without addition of any reagents from outside, it is possible to complete all the operations in a closed state once a sample, the necessary amplification reagents and the nucleic acid probe of the present invention are put into a reaction vessel.

Now, a mode of carrying out the present invention will be described by referring to Examples. However, the present invention is by no means restricted to these Examples. For base numbers of HCV RNA, the base numbers of HCV cDNA disclosed in Kato et al. (Proc. Natl. Acad. Sci. USA (1990) 87, 9524–9528) should be referred to.

EXAMPLE 1

Figure 1:
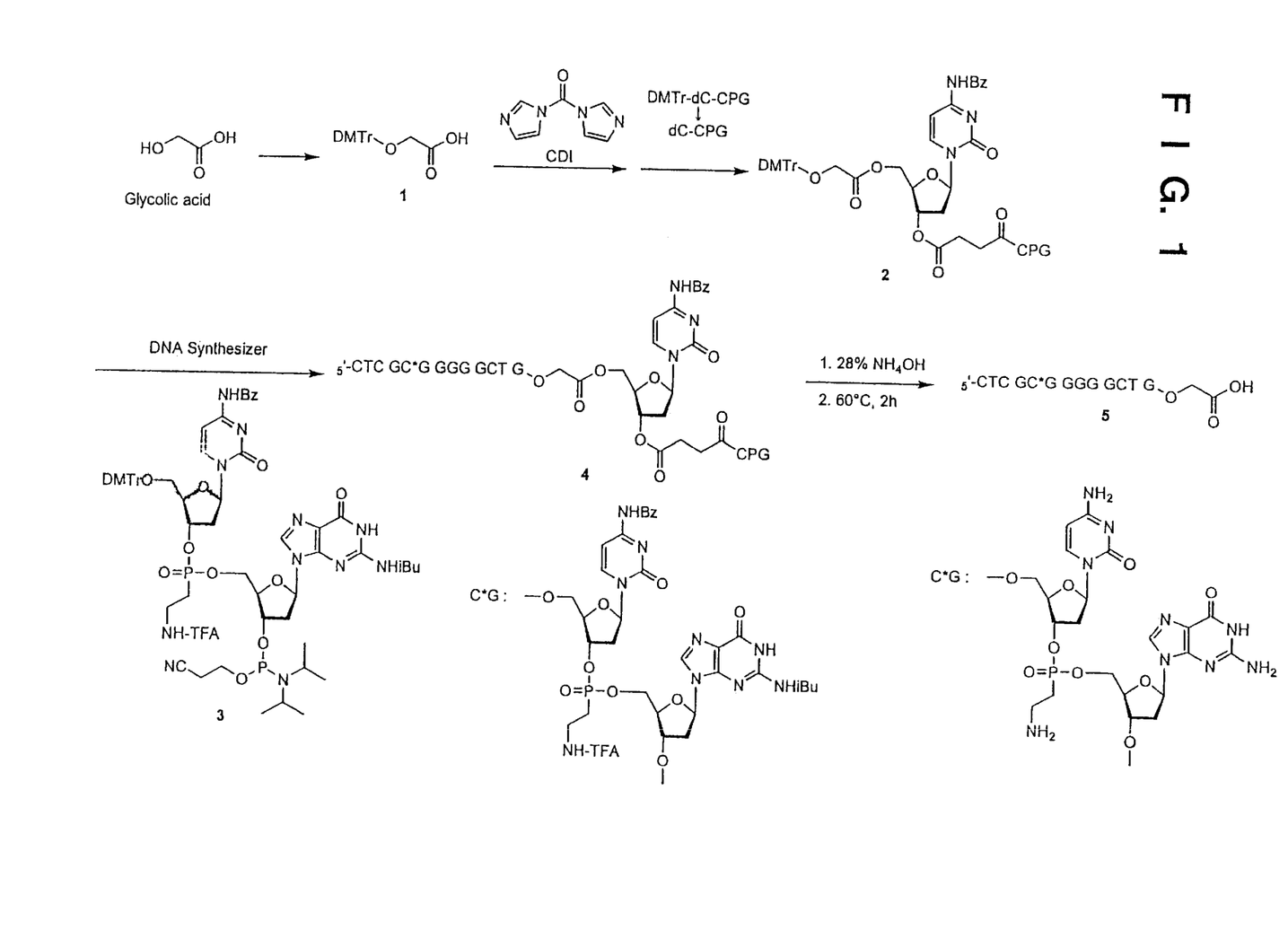
FIG. 1 is a scheme showing preparation of compounds obtained in Example 1.
Figure 2:
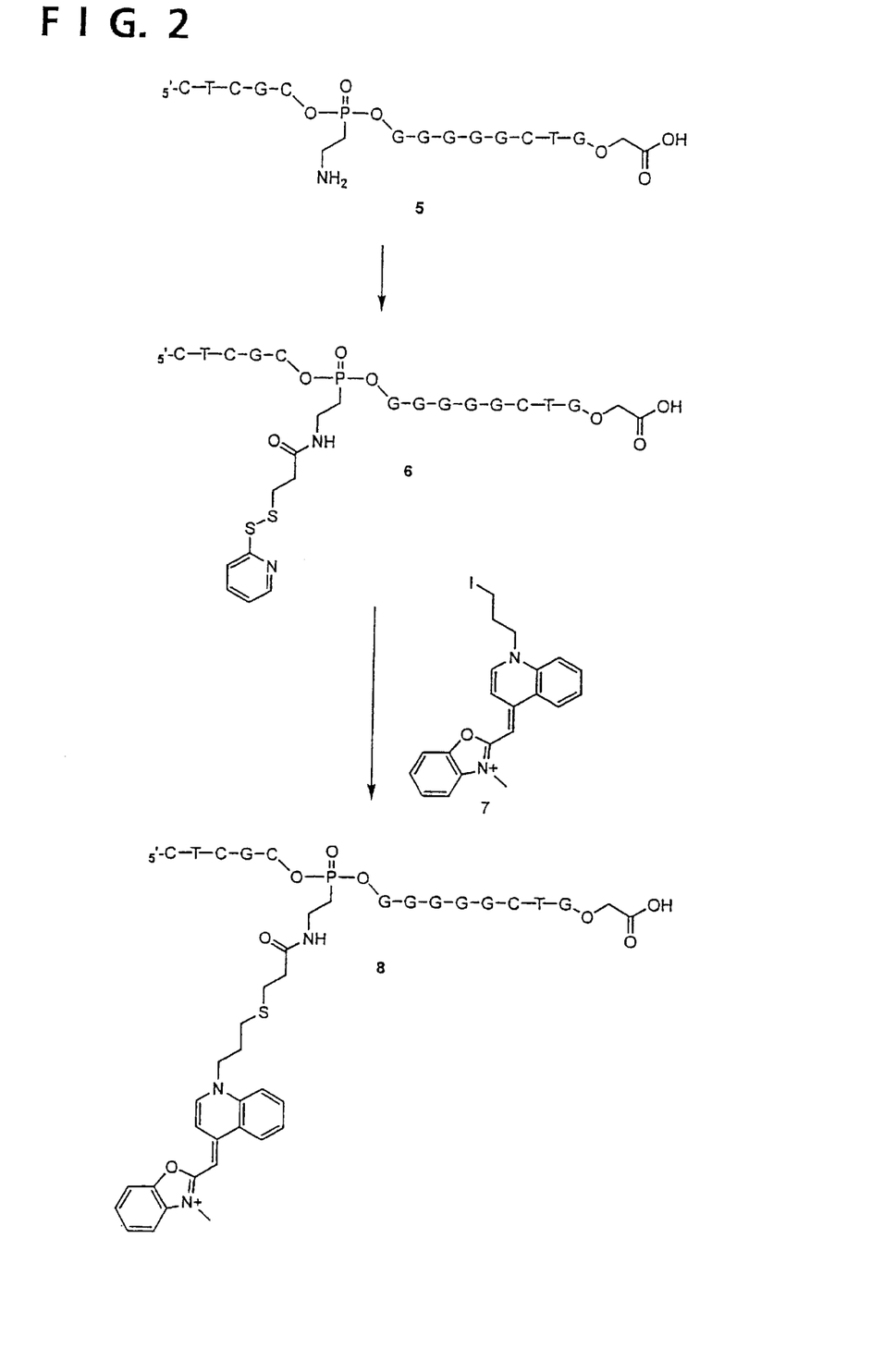
FIG. 2 is a scheme showing preparation of compounds obtained in Example 1.

Preparation of 3'-Glycolic Acid Modified Nucleic Acid Probe (FIG. 1 and FIG. 2)

(1) Preparation of DMTr-Glycolic Acid (Compound 1 in FIG. 1)

DMTr-Glycolic acid was prepared from Glycolic acid (0.078 g, 1.03 mmol). Glycolic acid was dissolved in 2 ml of DMF and stirred together with diisopropylethylamine (0.55 ml, 3.16 mmol) and DMTr-Cl (0.382 g, 1.13 mmol) at room temperature overnight. The reaction solution was concentrated to dryness and purified through a silica gel column to give 0.249 g of DMTr-Glycolic acid (Compound 1) as intended in a 64% yield.

(2) Preparation of DMTr-Glycolyl-CPG (Compound 2 in FIG. 1)

Trichloroacetic acid in methylene chloride was passed through a column packed with DMTr-dC CPG (1 μmol, Perkin-Elmer) to remove DMTr groups. The column was washed with anhydrous acetonitrile, loaded with DMTr-Glycolic acid (Compound 1, 0.104 g, 0.275 mmol) and carbonyldiimidazole (44 mg, 0.27 mmol) in 1 ml of THF, then sealed and left overnight. After the reaction, the column was washed with THF and treated with acetic anhydride and methylimidazole-THF for acetylation of the unreacted hydroxyl groups to give DMTr-Glycolly-CPG (Compound 2).

(3) Preparation of 3'-Glycolic Acid Modified Nucleic Acid Probe (Compound 5 in FIG. 1)

A synthetic oligonucleotide (Compound 4) of SEQ ID NO:1 was prepared by using compound 2 prepared above (DMTr-Glycolly-CPG) as the solid phase and CG amidite dimer (Compound 3) and G, C, T amidites as the starting materials by a DNA synthesizer (Perkin-Elmer, DNA synthesizer Model 391). In SEQ ID NO:1, a linker is linked between the cytosine and guanine at the 5th and 6th positions from the 5' end.

The resulting oligonucleotide of SEQ ID NO:1 was eluted with 28% $NH_4OH$ from the CPG column and heated at 60° for 2 hours for deprotection. The resulting synthetic oligonucleotide (Compound 5) was purified by HPLC (TSK gel ODS-120T, Tosoh Corporation) and lyophilized. Yield 18.2 OD, 159 nmol.

As shown in FIG. 2, Compound 5 (18.2 OD) thus obtained was dissolved in 50 μl distilled water and mixed with 50 μl of 0.2 M $Na_2HPO_4$ and 100 μl of 5% SPDP (N-succinimidyl-3-(2-pyridyldithio)propionate)/DMSO solution. After 2 hours of standing at room temperature, the reaction solution was diluted with 0.5 ml of distilled water and washed with chloroform. The aqueous layer was concentrated, desalted by gel filtration and purified by HPLC (TSK gel ODS-120T, Tosoh Corporation) to give Compound 6. Yield 2.4 OD, 21 nmmol.

Compound 6 (2.4 OD) was lyophilized, and the residue was dissolved in 200 μl of distilled water, mixed with 20 μl of 1M Tris-HCl (pH 5.1) and 20 μl of 1M DTT (dithiothreitol) and allowed to stand for 30 minutes. The DTT-treated reaction solution was mixed with a 200 μl portion of a solution of Compound 7 (1 mg) in a mixture of 200 μl of DMF, 600 μl of distilled water and 200 μl of 0.5M $Na_2HPO_4$ (pH 9.5) and allowed to stand at room temperature for 1 hour. The reaction solution was washed with butanol and concentrated, and ethanol was added to precipitate the crude product. The precipitated was purified by HPLC (TSK gel ODS-120T, Tosoh Corporation) to give 3'-Glycolic acid modified fluorescent probe (Compound 8) as intended. Yield 0.43 OD, 3.74 nmol.

EXAMPLE 2

Figure 3:
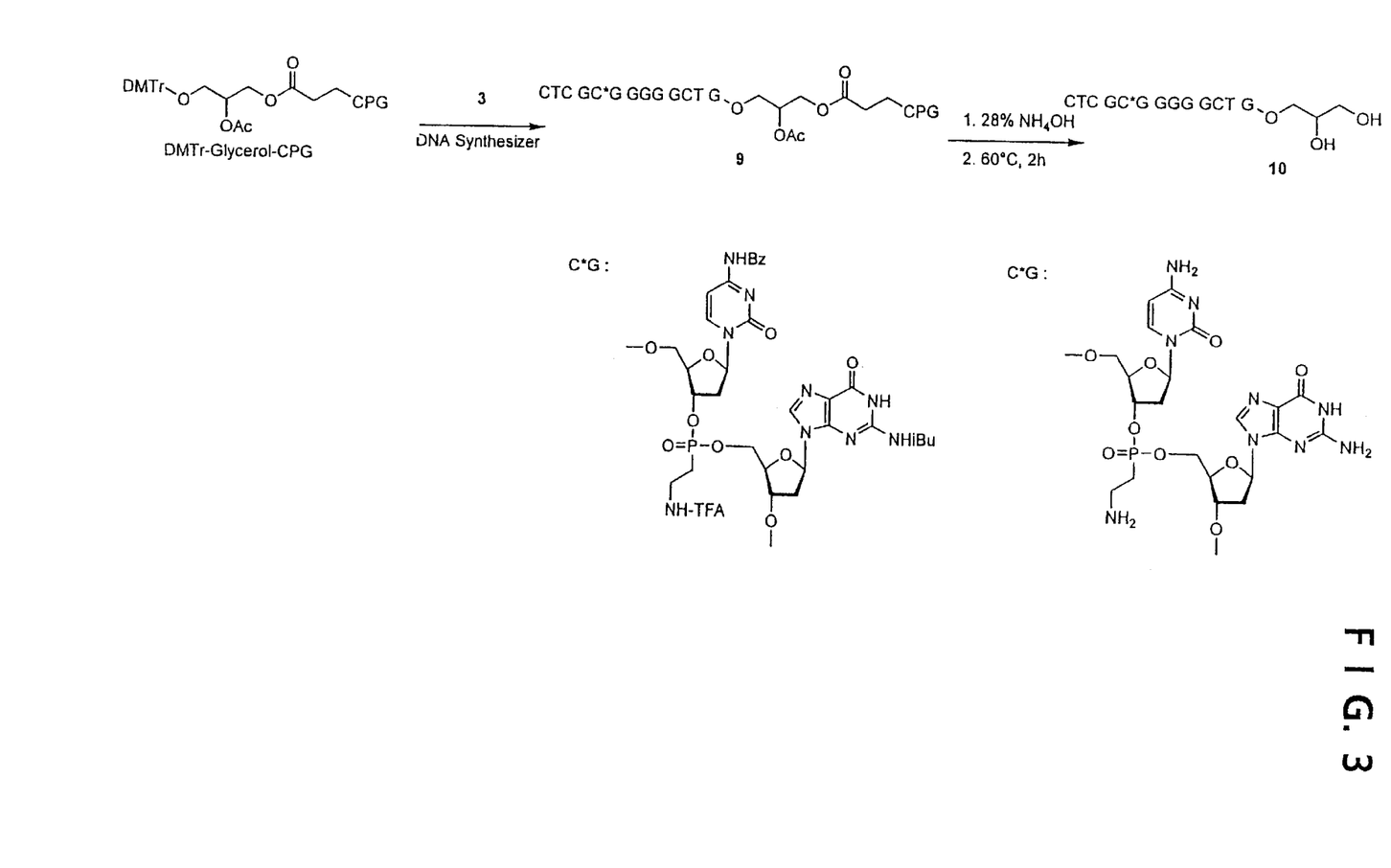
FIG. 3 is a scheme showing preparation of compounds obtained in Example 2.
Figure 4:
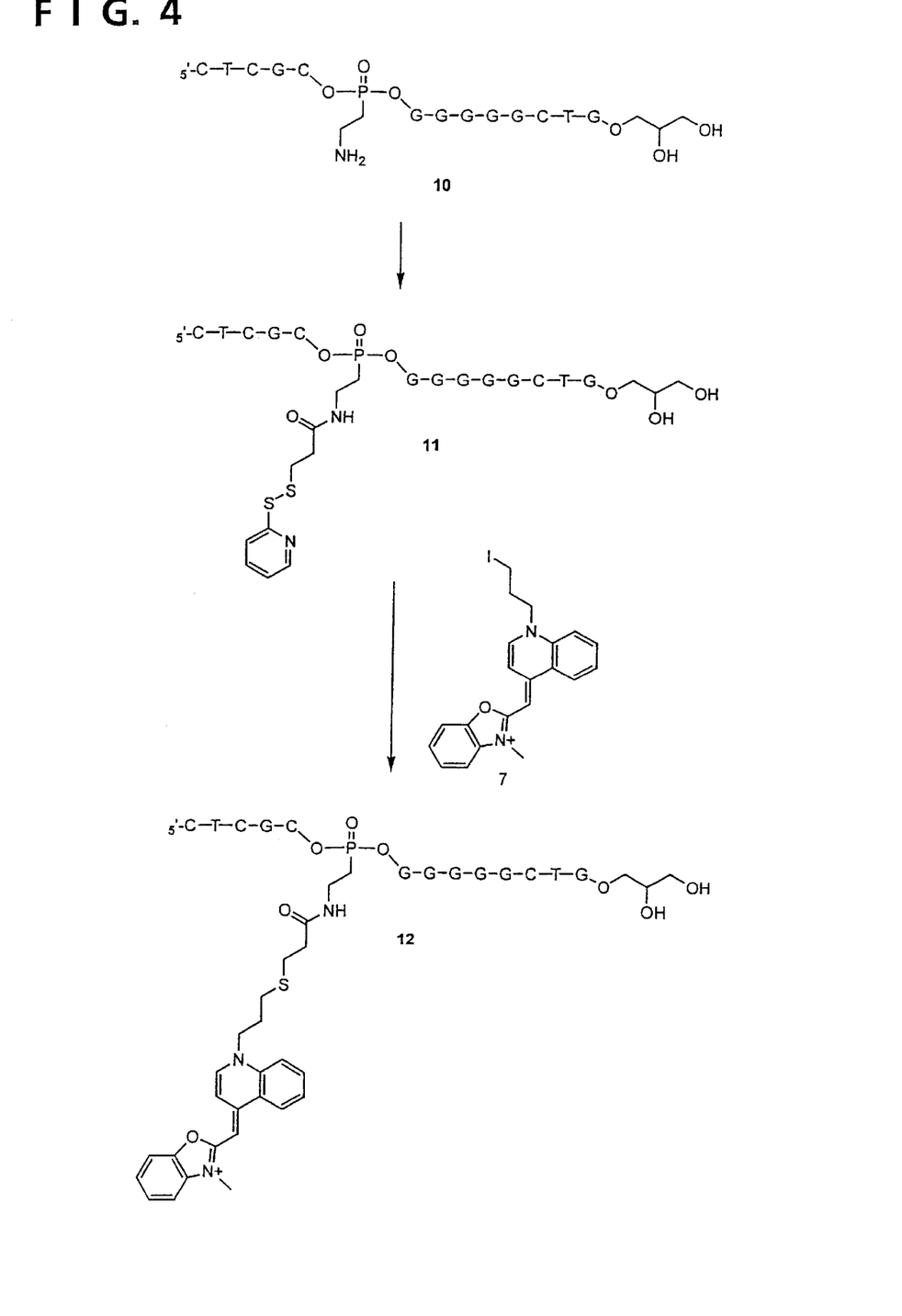
FIG. 4 is a scheme showing preparation of compounds obtained in Example 2.

Preparation of 3'-Glycerol Modified Nucleic Acid Probe (Compound 12) (FIG. 3 and FIG. 4)

As shown in FIG. 3, a synthetic oligonucleotide of SEQ ID NO:2 (Compound 9) was prepared by using DMTr-Glycerol-CPG (0.2 μmol×2, Peninsula Laboratories, Inc.) as the solid phase and above-mentioned Compound 3 and G, C, T amidites as the starting materials by a DNA synthesizer (Perkin-Elmer, DNA Synthesizer Model 391). In SEQ ID NO:2, a linker is linked between the cytosine and guanine at the 5th and 6th positions from the 5' end.

The resulting oligonucleotide of SEQ ID NO:2 (Compound 9) was eluted with 28% $NH_4OH$ from the CPG column and heated at 60° for 2 hours for deprotection. The resulting synthetic oligonucleotide (Compound 10) was purified by HPLC (TSK gel ODS-120T, Tosoh Corporation) and lyophilized. Yield 3.75 OD, 33 nmol. Among the 13 bases in the synthetic oligonucleotide of SEQ ID NO:2, the 11 bases from the 5'-end are complementary to the after-mentioned target nucleic acid.

As shown in FIG. 4, Compound 10 (OD 3.75) thus obtained was dissolved in 50 μl distilled water and mixed with 50 μl of 0.2 M $Na_2HPO_4$ and 100 μl of 5% SPDP/DMSO solution. After 2 hours of standing at room temperature, the reaction solution was diluted with 0.5 ml of distilled water and washed with chloroform. The aqueous layer was concentrated, desalted by gel filtration and purified by HPLC (TSK gel ODS-120T, Tosoh Corporation) to give Compound 11. Yield 0.10 OD, 0.87 nmmol.

Compound 11 (0.11 OD) was lyophilized, and the residue was dissolved in 200 μl of distilled water, mixed with 20 μl of 1M Tris-HCl (pH 5.1) and 20 μl of 1M DTT and allowed to stand for 30 minutes. The DTT-treated reaction solution was mixed with a 200 μl portion of a solution of above-mentioned Compound 7 (1 mg) in a mixture of 200 μl of DMF, 600 μl of distilled water and 200 μl of 0.5M $Na_2HPO_4$ (pH 9.5) and allowed to stand at room temperature for 1 hour. The reaction solution was washed with butanol and concentrated, and ethanol was added to precipitate the crude product. The precipitated was purified by HPLC (TSK gel ODS-120T, Tosoh Corporation) to give 3'-Glycerol modified nucleic acid probe (Compound 12) as intended. Yield 0.018 OD, 0.16 nmol.

EXAMPLE 3

The following procedure for HCV RNA amplification at constant temperature was done with a positive sample (containing a standard HCV RNA as the target nucleic acid (a RNA consisting of bases 113 to 267 in HCV RNA)) or a negative sample (not containing the target nucleic acid) in the presence of a fluorescent intercalative dye-labeled nucleic acid probe (Compound 8), and the change in the fluorescent signal was measured.

18.25 μl of a reaction solution having the following composition was poured into each PCR tube.

1.20 μl 1M Tris-acetate (pH 8.1)
0.40 μl 1M magnesium acetate
1.88 μl 2M potassium acetate
8.00 μl 60% sorbitol
0.60 μl DMSO (dimethyl sulfoxide)
3.00 μl 100 mM DTT (dithiothreitol)
1.50 μl 20 mM dATP, dGTP, dCTP and dTTP
0.30 μl 20 μM promoter primer (SEQ ID NO:3; containing bases 113 to 137 in HCV RNA)
0.30 μl 20 μM antisense primer (SEQ ID NO:4; single-stranded oligo DNA complementary to bases 248 to 267 in HCV RNA)
1.07 μl deionized water 50 μl of mineral oil was laid over the reaction solution, and 4 μl of the standard HCV RNA (1000 copies/4 μl) as the positive sample or TE buffer as the negative sample was added. Then, reaction was carried out at 50° C. for 5 minutes. After the reaction, 5.25 μl of a reaction solution having the following composition was added.

3.40 μl 50 U/μl SP6 RNA polymerase
1.24 μl 34 U/μl AMV reverse transcriptase
0.15 μl 20 mg/ml BSA
0.46 μl 130 U/μl RNase inhibitor Subsequent to the addition of the reaction solution, reaction was carried out at 50° C. for 5 minutes. Further, 1.50 μl of 20 mM of ATP, GTP, CTP and UTP were added each, and reaction was carried out at 50° C. for 5 minutes. Then, 1.00 μl of 0.75 μM 3'-Glycolic acid modified nucleic acid probe (Compound 8), and the fluorescent intensity was measured by a fluorescent detector (excitation wavelength; 490 nm, emission wavelength; 510 nm) at 5-minute intervals starting from the addition of ATP, GTP, CTP and UTP.

Figure 5:
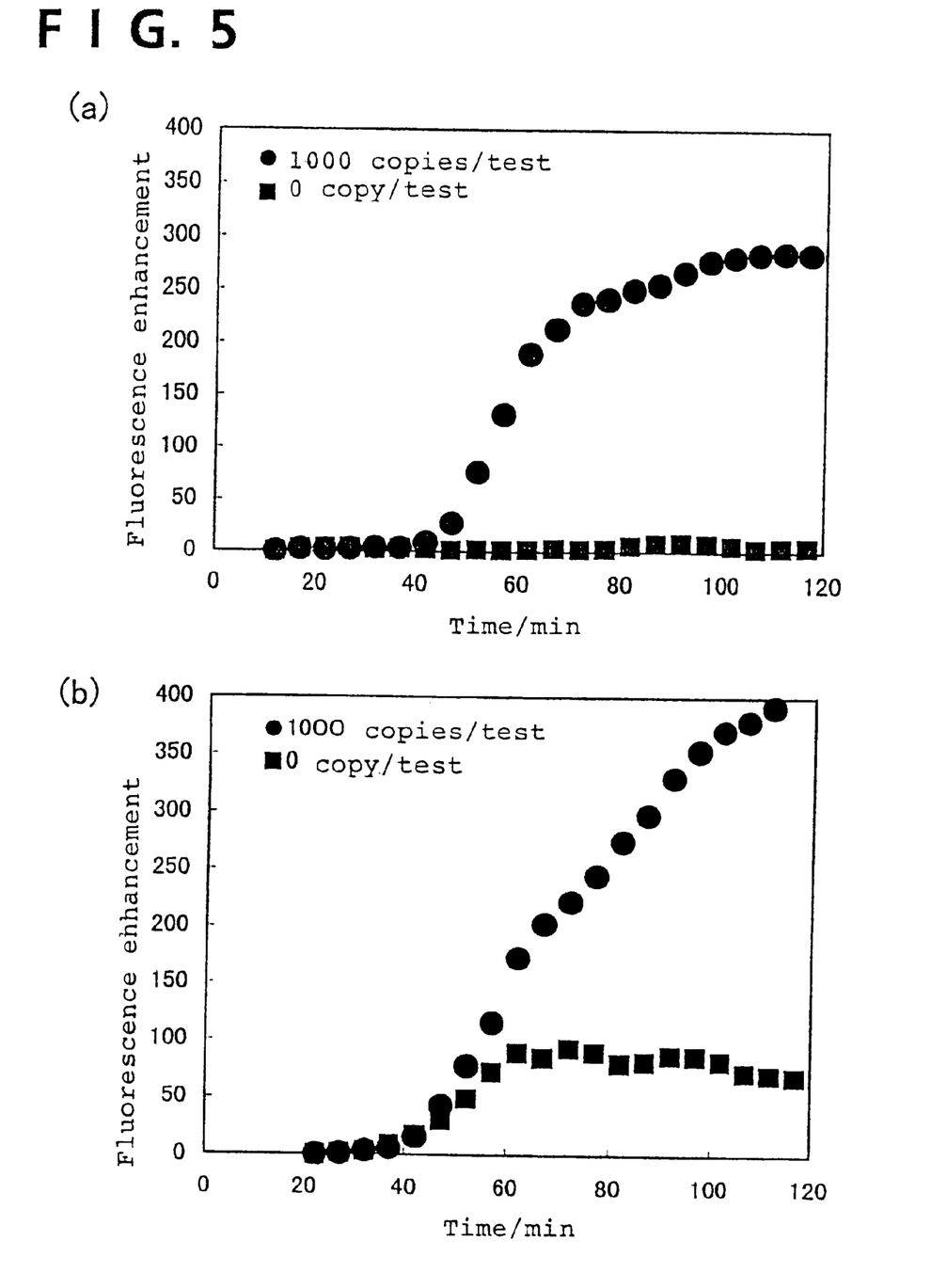
FIG. 5 shows the results of the measurement in Example 3. The fluorescent intensity of the positive sample (solid circle) showed a time-dependent increase while the fluorescent intensity of the negative sample (solid square) scarcely increased.

The time course of the fluorescent intensity thus obtained is shown in FIG. 5(a). With the negative sample, the fluorescent intensity scarcely increased during the 120 minute' measurement, while with the positive sample, the fluorescent intensity began to increase at about 50 minutes and reached a plateau at about 100 minutes.

For comparison, the same procedure was done with a nucleic acid probe obtained from the synthetic oligonucleotide of SEQ ID NO:5. The results are shown in FIG. 5(b). The probe used for comparison is the same as abovementioned 3'-Glycolic acid modified nucleic acid probe except that it has a different 3'-end sequence and is not modified at the 3' end.

FIG. 5(b) shows that with the probe which is not complementary to the target nucleic acid at the 3' end and is not modified at the 3' end, though the fluorescent intensity of the positive sample showed a time-dependent increase, the fluorescent intensity of the negative sample as the background fluorescence increased during the 120 minute' measurement.

These results demonstrate that in amplification of a nucleic acid in the presence of a fluorescent intercalative dye-linked DNA probe, a nucleic acid probe having a 3'-modification like 3'-Glycolic acid modification is effective to improve the sensitivity and precision by preventing amplification of the nucleic acid probe itself or reducing the background signal.

By virtue of the chemical modification at the 3' end, the nucleic acid probe of the present invention does not undergo nucleic acid elongation reaction from the 3' end even if it is present during amplification of a nucleic acid involving synthesis of a complementary nucleic acid using a target nucleic acid as the template such as DNA or RNA amplification. Therefore, once the reagents necessary for amplification of a target nucleic acid and the nucleic acid probe of the present invention necessary for measurement of the target nucleic acid are put into a reaction vessel, it is possible to complete all the operations while keeping the reaction vessel sealed. Consequently, it is possible to assay a target nucleic acid with high specificity and sensitivity without the possibility of contamination of other samples due to generation of aerosol by combining the nucleic acid probe with various methods for amplification of a target nucleic acid.

What is claimed is:

1. A nucleic acid probe which is a single-stranded nucleic acid complementary to a specific nucleic acid sequence and is labeled so as to give off a measurable fluorescent signal on hybridization with a nucleic acid containing the specific nucleic acid sequence, wherein the 3' end of the probe is modified as represented by the following formula (1):

(1)

wherein R is —COOH, —CONH$_2$, —(CH$_2$)$_n$OH, —CH(OH)—CH$_2$OH, or —CH[(CH$_2$)$_n$—NHR$_1$]—CH$_2$OH, R$_1$ is H, a dye, or an amino protecting group, and n is an integer of at least 1, wherein the single-stranded nucleic acid is DNA having an oxygen atom retained at position 3 of the deoxyribose moiety.

2. A method for assay of a target nucleic acid containing a specific base sequence, which comprises amplifying the target nucleic acid in the presence of a single-stranded nucleic acid probe complementary to the specific nucleic acid sequence which is labeled so as to give off a measurable signal on hybridization with a nucleic acid containing the specific nucleic acid sequence and detecting or quantifying the specific nucleic acid by using hybridization of the amplified target nucleic acid with the nucleic acid probe during and/or after the amplification, wherein the 3' end of the single-stranded nucleic acid probe is modified as represented by the following formula (2):

(2)

wherein R is —COOH, —CONH$_2$, —(CH$_2$)$_n$OH, —CH(OH)—CH$_2$OH, or —CH[(CH$_2$)$_n$—NHR$_1$]—CH$_2$OH, R$_1$ is H, a dye, or an, and n is an integer of at least 1, wherein the single-stranded nucleic acid is DNA having an oxygen atom retained at position 3 of the deoxyribose moiety.

3. A process for preparing the nucleic acid probe of claim 1 comprising the steps of:

synthesizing a DNA oligomer complementary to the specific nucleic acid sequence by a DNA synthesizer using a solid phase represented by the formula (3)

(3)

or the formula (4)

(4)

wherein R$_2$ and R$_3$ are hydroxyl-protecting groups, R$_4$ is —(CH$_2$)$_n$—, —CH(OH)—CH$_2$—, or —CH[(CH$_2$)$_n$—NHR$_5$]—CH$_2$—, R$_5$ is H, a dye, or an amino protecting group, n is an integer of at least 1, S is a support, and X is an arbitrary linker, releasing from the support the DNA oligomer having a modified 3'-end of formula (5)

(5)

wherein R is —COOH, —CONH$_2$, —(CH$_2$)$_n$OH, —CH(OH)—CH$_2$OH, or —CH[(CH$_2$)$_n$—NHR$_1$]—CH$_2$OH, R$_1$ is H, a dye, or an amino protecting group, and n is an integer of at least 1, and linking the DNA oligomer having the modified 3'-end to a fluorescent intercalative dye.

4. The nucleic acid probe made by the process of claim 3.

5. The nucleic acid probe of claim 1, wherein the single-stranded nucleic acid is DNA having a backbone containing phosphodiester linkages between adjacent nucleotides.

6. The method for assay of claim 2, wherein the single-stranded nucleic acid probe is DNA having a backbone containing phosphodiester linkages between adjacent nucleotides.

7. The nucleic acid probe of claim 1 wherein the amino protecting group is Fmoc.

8. A process for preparing the nucleic acid probe of claim 7 comprising the steps of:

synthesizing a DNA oligomer complementary to the specific nucleic acid sequence by a DNA synthesizer using a solid phase represented by the formula (3)

(3)

or the formula (4)

(4)

wherein $R_2$ and $R_3$ are hydroxyl-protecting groups, $R_4$ is —$(CH_2)_n$—, —CH(OH)—$CH_2$—, or —CH[$(CH_2)_n$—$NHR_5$]—$CH_2$—, $R_5$ is Fmoc, n is an integer of at least 1, S is a support, and X is an arbitrary linker, releasing from the support the DNA oligomer having a modified 3'-end of formula (5)

(5)

wherein R is —COOH, —$CONH_2$, —$(CH_2)_n OH$, —CH(OH)—$CH_2OH$, or —CH[$(CH_2)_n$—$NHR_1$]—$CH_2OH$, $R_1$ is Fmoc, and n is an integer of at least 1, and linking the DNA oligomer having the modified 3'-end to a fluorescent intercalative dye.

9. The nucleic acid probe made by the process of claim 8.

10. The nucleic acid probe of claim 7, wherein the single-stranded nucleic acid is DNA having a backbone containing phosphodiester linkages between adjacent nucleotides.

11. The method of claim 2 wherein the amino protecting group is Fmoc.

12. The method for assay of claim 11, wherein the single-stranded nucleic acid probe is DNA having a backbone containing phosphodiester linkages between adjacent nucleotides.

* * * * *

SEQUENCE LISTING

<160> NUMBER OF SEQ ID NOS: 5

<210> SEQ ID NO 1
<211> LENGTH: 13
<212> TYPE: DNA
<213> ORGANISM: Artificial Sequence
<220> FEATURE:
<223> OTHER INFORMATION: Synthesized oligonucleotide

<400> SEQUENCE: 1
ctcgcggggg ctg                                                                13

<210> SEQ ID NO 2
<211> LENGTH: 50
<212> TYPE: DNA
<213> ORGANISM: Artificial Sequence
<220> FEATURE:
<223> OTHER INFORMATION: Synthesized oligonucleotide

<400> SEQUENCE: 2
atttaggtga cactatagaa tacaacctcc cgggagagcc atagtggtct                        50

<210> SEQ ID NO 3
<211> LENGTH: 50
<212> TYPE: DNA
<213> ORGANISM: Artificial Sequence
<220> FEATURE:
<223> OTHER INFORMATION: Synthesized Promoter_Eprimer

<400> SEQUENCE: 3
atttaggtga cactatagaa tacaacctcc cgggagagcc atagtggtct                        50

<210> SEQ ID NO 4
<211> LENGTH: 20
<212> TYPE: DNA
<213> ORGANISM: Artificial Sequence
<220> FEATURE:
<223> OTHER INFORMATION: Synthesized Antisnese_Eprimer -continued

```
<400> SEQUENCE: 4
gcctttcgcg acccaacact                                              20

<210> SEQ ID NO 5
<211> LENGTH: 16
<212> TYPE: DNA
<213> ORGANISM: Artificial Sequence
<220> FEATURE:
<223> OTHER INFORMATION: Synthesized oligonucleotide

<400> SEQUENCE: 5
ctcgcggggg cttttt                                                  16
```